United States Patent
Takashino et al.

(10) Patent No.: US 10,034,703 B2
(45) Date of Patent: Jul. 31, 2018

(54) CONTROL DEVICE FOR ENERGY TREATMENT TOOL, AND ENERGY TREATMENT SYSTEM

(71) Applicant: OLYMPUS CORPORATION, Hachioji-shi, Tokyo (JP)

(72) Inventors: Tomoyuki Takashino, Fuchu (JP); Yusuke Takei, Hino-shi (JP); Kazuhiro Tanaka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/265,142

(22) Filed: Sep. 14, 2016

(65) Prior Publication Data

US 2017/0000548 A1 Jan. 5, 2017

Related U.S. Application Data (63) Continuation of application No. PCT/JP2015/078212, filed on Oct. 5, 2015.

(30) Foreign Application Priority Data

Oct. 15, 2014 (JP) ................................. 2014-211034

(51) Int. Cl.
*A61B 18/08* (2006.01)
*A61B 18/04* (2006.01)
*A61B 18/00* (2006.01)

(52) U.S. Cl.
CPC ............ *A61B 18/082* (2013.01); *A61B 18/04* (2013.01); *A61B 18/085* (2013.01);
(Continued)

(58) Field of Classification Search
CPC ....... A61B 18/04; A61B 18/08; A61B 18/082; A61B 18/085; A61B 2018/00589;
(Continued)

(56) References Cited

U.S. PATENT DOCUMENTS 6,293,943 B1   9/2001 Panescu et al.
6,740,085 B2 *  5/2004 Hareyama ............ A61B 18/085
                                                              606/50

(Continued)

FOREIGN PATENT DOCUMENTS

JP    2005-253789 A    9/2005
WO    2010/070766 A1   6/2010
(Continued)

OTHER PUBLICATIONS

April 27, 2017 Notification of Transmittal of Translation of IPRP issued in International Application No. PCT/JP2015/078212.
Nov. 2, 2015 International Search Report issued in Patent Application No. PCT/JP2015/078212.
(Continued)

*Primary Examiner* — Michael Peffley
*Assistant Examiner* — Khadijeh Vahdat
(74) *Attorney, Agent, or Firm* — Oliff PLC (57) ABSTRACT

A control device is a control device for an energy treatment tool including a first holding member and a second holding member which hold a biological tissue, and a heating element configured to generate heat corresponding to supplied power, thereby heating a holding surface. The control device includes a temperature acquiring section that acquires a temperature of the heating element; and a surface temperature estimating section that estimates, as a surface temperature, a temperature of at least a part of a surface of the first holding member which is different from a portion facing the second holding member, based on a change of the temperature of the heating element after supply of the power is stopped.

11 Claims, 6 Drawing Sheets

(52) U.S. Cl.
CPC ............... *A61B 2018/00589* (2013.01); *A61B 2018/00642* (2013.01); *A61B 2018/00678* (2013.01); *A61B 2018/00696* (2013.01); *A61B 2018/00708* (2013.01); *A61B 2018/00714* (2013.01); *A61B 2018/00791* (2013.01); *A61B 2018/00803* (2013.01); *A61B 2018/00821* (2013.01)

(58) Field of Classification Search
CPC ........... A61B 2018/00642; A61B 2018/00678; A61B 2018/00696; A61B 2018/00708; A61B 2018/00714; A61B 2018/00791; A61B 2018/00803; A61B 2018/00821
USPC .............................. 606/51–52, 169, 205–207
See application file for complete search history.

(56) References Cited

U.S. PATENT DOCUMENTS

| 2002/0082593 | A1 | 6/2002 | Hareyama et al. |
| 2013/0245619 | A1 | 9/2013 | Yasunaga |

FOREIGN PATENT DOCUMENTS

| WO | 2012/081514 A1 | 6/2012 |
| WO | 2014/076621 A1 | 5/2014 |

OTHER PUBLICATIONS

Jun. 4, 2018 Extended European Search Report issued in European Patent Application No. 15850852.3.

* cited by examiner

CONTROL DEVICE FOR ENERGY TREATMENT TOOL, AND ENERGY TREATMENT SYSTEM

CROSS-REFERENCE TO RELATED APPLICATIONS

This application is a Continuation Application of PCT Application No. PCT/JP2015/078212, filed Oct. 5, 2015 and based upon and claiming the benefit of priority from prior Japanese Patent Application No. 2014-211034, filed Oct. 15, 2014, the entire contents of all of which are incorporated herein by reference.

BACKGROUND OF THE INVENTION

1. Field of the Invention

The present invention relates to a control device for an energy treatment tool, and an energy treatment system.

2. Description of the Related Art

There is known a surgical treatment tool which holds a biological tissue to apply heat energy to the biological tissue, thereby performing a treatment to coagulate or incise the biological tissue. For example, in Jpn. Pat. Appln. KOKAI Publication No. 2005-253789, a surgical treatment tool is disclosed in which a heating element having a resistance heating pattern is disposed in forceps.

In such a treatment tool as mentioned above, it is preferable that in a holding portion holding the biological tissue, a temperature of a holding surface that comes in contact with the biological tissue only rises and a temperature of a portion other than the holding surface does not rise. However, when the treatment to the biological tissue is repeatedly performed, the temperature of the portion other than the holding surface in the holding portion also rises.

BRIEF SUMMARY OF THE INVENTION

According to an aspect of the invention, a control device for an energy treatment tool comprising a first holding member configured so that a holding surface comes in contact with a biological tissue, a second holding member that is configured to open and close relatively to the first holding member to hold the biological tissue between the first holding member and the second holding member, and a heating element configured to generate heat corresponding to supplied power, thereby heating the holding surface, includes a temperature acquiring section that acquires a temperature of the heating element; and a surface temperature estimating section that estimates, as a surface temperature, a temperature of at least a part of a surface of the first holding member which is different from a portion facing the second holding member, based on a change of the temperature of the heating element after supply of the power is stopped.

According to an aspect of the invention, an energy treatment system includes the control device; and an energy treatment tool comprising the first holding member, the second holding member, and the heating element.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
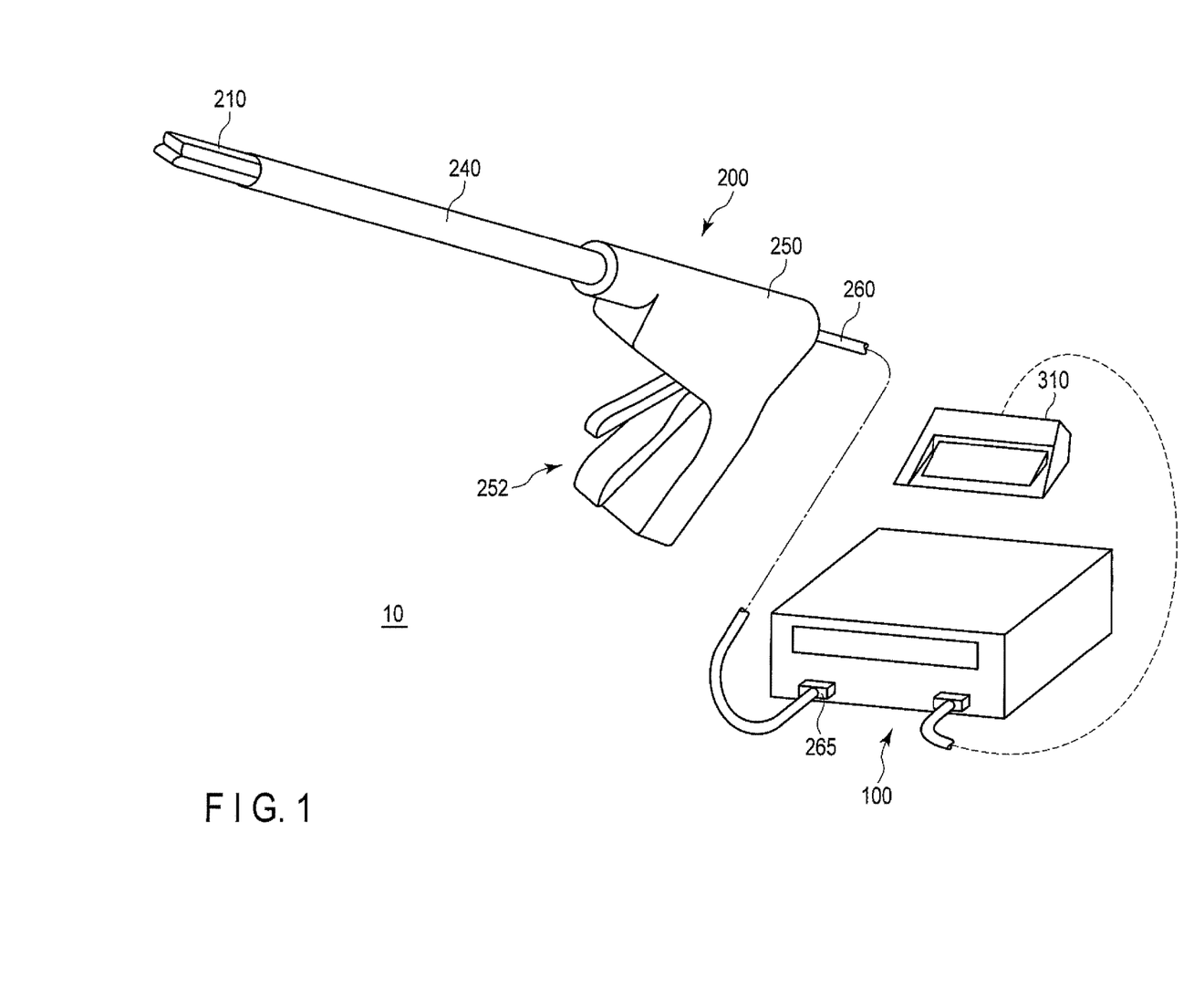
FIG. 1 is a view showing an outline of a configuration example of an energy treatment system according to one embodiment.

One embodiment of the present invention will be described with reference to the drawings. FIG. 1 shows one example of a configuration example of an energy treatment system according to the present embodiment. An energy treatment system 10 is a device for use in a medical treatment of a biological tissue. The energy treatment system 10 applies heat energy to the biological tissue. The energy treatment system 10 comprises a control device 100, an energy treatment tool 200, and a foot switch 310.

The energy treatment tool 200 is, for example, a linear type of treatment tool for a surgical treatment which is passed through an abdominal wall to perform a treatment. The energy treatment tool 200 has a handle 250, a shaft 240 attached to the handle 250, and a holding portion 210 disposed at a distal end of the shaft 240. The holding portion 210 is openable and closable to hold the biological tissue of a treatment target, thereby performing a treatment such as coagulation or incision of the biological tissue. Hereinafter, for the description, a holding portion 210 side will be referred to as a distal side and a handle 250 side will be referred to as a proximal side. The handle 250 comprises operation knobs 252 to operate the holding portion 210. Furthermore, in the handle 250, there is disposed an unshown memory to store a proper value or the like concerned with the energy treatment tool 200. It is to be noted that needless to say, a shape of the energy treatment tool 200 mentioned herein is one example, and the tool may have another shape as long as the tool has a similar function.

The handle 250 is connected to a control device 100 via a cable 260. Here, the cable 260 is connected to the control device 100 by a connector 265, and this connection is removable. That is, an energy treatment system 10 is configured so that the energy treatment tool 200 can be changed every treatment. The control device 100 is connected to the foot switch 310. The foot switch 310 to be operated by foot may be replaced with a switch to be operated by hand or another switch. An operator operates a pedal of the foot switch 310, thereby switching on/off supply of energy from the control device 100 to the energy treatment tool 200.

Figure 2:
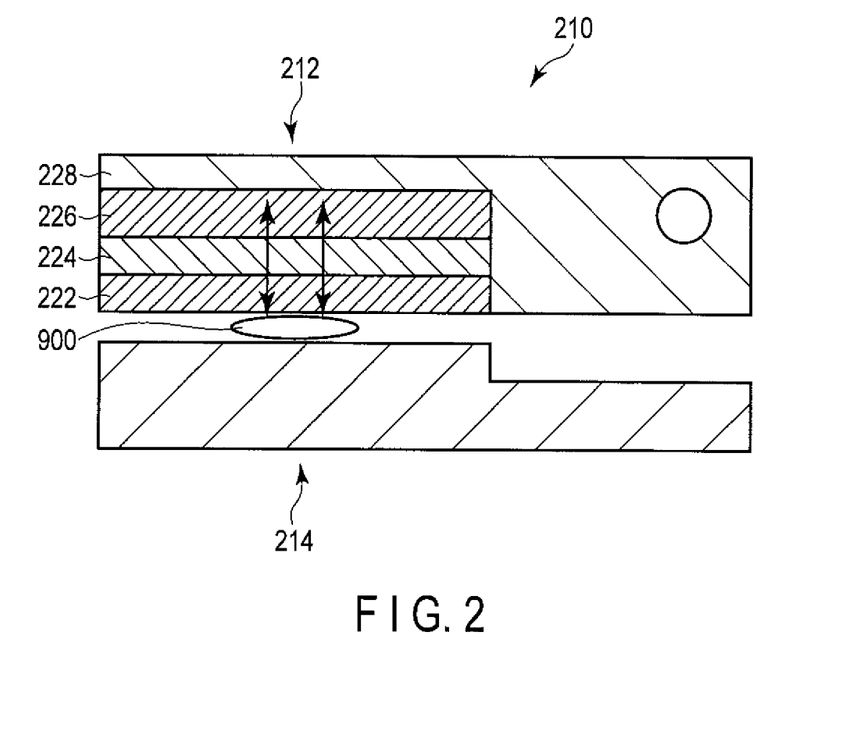
FIG. 2 is a schematic view showing an outline of a configuration example of a holding portion according to the one embodiment.

An outline of a configuration example of the holding portion 210 will be described with reference to FIG. 2 of a configuration view. The holding portion 210 has a first holding member 212 and a second holding member 214. The first holding member 212 and the second holding member 214 are relatively displaced and a biological tissue 900 is held between the first holding member 212 and the second holding member 214. A surface of the first holding member 212 which faces the second holding member 214 and comes in contact with the biological tissue is referred to as a holding surface. Furthermore, a surface opposite to the holding surface of the first holding member 212 is referred to as a back surface.

A treating portion 222 made of a metal having a good thermal conductivity, e.g., copper is disposed in the holding surface of the first holding member 212. On a back surface side of the treating portion 222, a heating element 224 is disposed. The heating element 224 includes a resistance pattern that is a lead wire having a high electric resistance, and generates heat when a current flows through the resistance pattern. On a back surface side of the heating element 224, there is disposed an insulating member 226 made of a material having a low thermal conductivity. In the first holding member 212, a portion other than the treating portion 222, the heating element 224 and the insulating member 226 is defined as a holding member main body 228.

When power is supplied to the heating element 224, the heating element 224 generates heat. The heat generated by the heating element 224 is transferred through the treating portion 222 having a high thermal conductivity to heat the biological tissue 900. Furthermore, the heat generated by the heating element 224 is insulated by the insulating member 226 having a low thermal conductivity, but a part of the heat is transferred to the back surface of the first holding member 212 via the insulating member 226. For example, the back surface of the first holding member 212 is a portion having the possibility of coming into contact with a tissue other than the treatment target, when the energy treatment tool 200 is used. There is a possibility that the tissue other than the treatment target is heated to damage the tissue when a temperature of the back surface becomes a high temperature. Therefore, it is necessary to acquire the temperature of the back surface and maintain the temperature of the back surface at a temperature that is not high. Here, the temperature that is not high is a temperature at which, for example, protein is not denatured.

Figure 3:
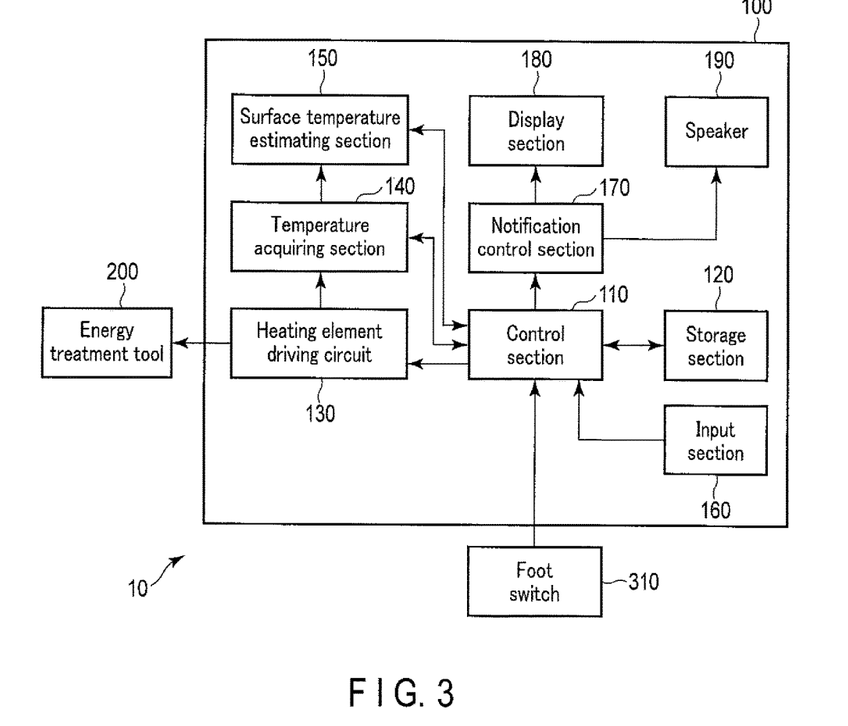
FIG. 3 is a block diagram showing an outline of a configuration example of the energy treatment system according to the one embodiment.

An outline of a configuration example of the control device 100 will be described with reference to FIG. 3. The control device 100 has a control section 110, a storage section 120, a heating element driving circuit 130, a temperature acquiring section 140, a surface temperature estimating section 150, an input section 160, a notification control section 170, a display section 180, and a speaker 190.

The control section 110 is connected to each section in the control device 100, and controls each section of the control device 100. The foot switch 310 is connected to the control section 110, and an on-signal indicating that the treatment by the energy treatment tool 200 is to be performed and an off-signal indicating that the treatment is to be stopped are input from the foot switch 310 to the control section. The control section 110 calculates the power to be applied to the heating element 224. The control section 110 causes the heating element driving circuit 130 to apply the calculated power into the heating element 224.

The storage section 120 includes, for example, a usual semiconductor memory. In the storage section 120, various types of programs, data and the like required for an operation of the control device 100 are stored. The control section 110 operates in accordance with, for example, the program stored in the storage section 120.

The heating element driving circuit 130 is connected to the energy treatment tool 200, and drives the heating element 224 of the energy treatment tool 200 under control of the control section 110. That is, the heating element driving circuit 130 supplies the power to the resistance pattern of the heating element 224 under the control of the control section 110.

The temperature acquiring section 140 has a function of acquiring voltage to be applied from the heating element driving circuit 130 to the heating element 224 and current at this time, and acquiring a resistance value of the resistance pattern of the heating element 224 on the basis of the voltage and the current. The resistance value of the resistance pattern changes in accordance with a temperature of the resistance pattern. The storage section 120 stores a relation between the temperature and the resistance value of the resistance pattern which is acquired beforehand. The temperature acquiring section 140 calculates the temperature of the resistance pattern on the basis of the acquired resistance value of the resistance pattern by use of the relation between the temperature and the resistance value of the resistance pattern. The temperature acquiring section 140 outputs the obtained temperature of the resistance pattern, i.e., the temperature of the heating element 224 to the surface temperature estimating section 150.

The surface temperature estimating section 150 estimates, as a surface temperature, a temperature of at least a part of the surface of the first holding member 212 excluding the surface of the first holding member 212 which faces the second holding member 214. Examples of the surface from which the surface temperature is estimated include a back surface and a side surface of the holding member main body 228. The surface temperature estimating section 150 acquires the temperature of the heating element 224 from the temperature acquiring section 140. The surface temperature estimating section 150 estimates the surface temperature on the basis of characteristics of a temperature decrease of the heating element 224 after stop of power supply to the heating element 224.

The input section 160 includes a usual input device such as a button, a knob or a keyboard. Various settings and the like of the control section 110 are input into the input section 160. The input section 160 outputs the input information to the control section 110. The notification control section 170 controls operations of the display section 180 and the speaker 190. The display section 180 displays various settings and the like of the control section 110. The speaker 190 outputs an alarm sound and the like.

The control section 110, the temperature acquiring section 140, the surface temperature estimating section 150, the notification control section 170 or the like includes, for example, a central processing unit (CPU) or an application specific integrated circuit (ASIC).

Next, an operation of the energy treatment system 10 according to the present embodiment will be described. The operator beforehand operates the input section 160 of the control device 100 to set output conditions of the energy treatment system 10, e.g., a target temperature, a heating time or the like of the heating by heat energy output. In the energy treatment system 10, respective values may individually be set, or setting of a set value in accordance with an operation system may be selected.

The holding portion 210 and the shaft 240 of the energy treatment tool 200 are inserted into, for example, an abdominal cavity through the abdominal wall. The operator operates the operation knobs 252 to open and close the holding portion 210 and holds the biological tissue of the treatment target by the first holding member 212 and the second holding member 214. At this time, the holding surface of the treating portion 222 of the first holding member 212 comes in contact with the biological tissue of the treatment target.

On holding the biological tissue of the treatment target by the holding portion 210, the operator operates the foot switch 310. When the foot switch 310 is switched on, the power is supplied from the control device 100 to the heating element 224 via the cable 260 so that a temperature of the holding surface of the first holding member 212 is the target temperature. Here, the target temperature is, for example, 200° C. The current at this time flows through the resistance pattern of the heating element 224 from the control device 100 via the cable 260. The resistance pattern of the heating element 224 generates heat by the current. The heat generated by the resistance pattern is conducted to the treating portion 222. As a result, a temperature of the treating portion 222 rises. Due to the temperature rise of the treating portion 222, the biological tissue that is in contact with the treating portion 222 is burnt out and coagulated. When the biological tissue is heated to coagulate, the output of the heat energy stops. It is to be noted that when the target temperature of the holding surface is, for example, 300° C., the biological tissue is cut at this high temperature. The treatment of the biological tissue is completed as described above.

Figure 4:
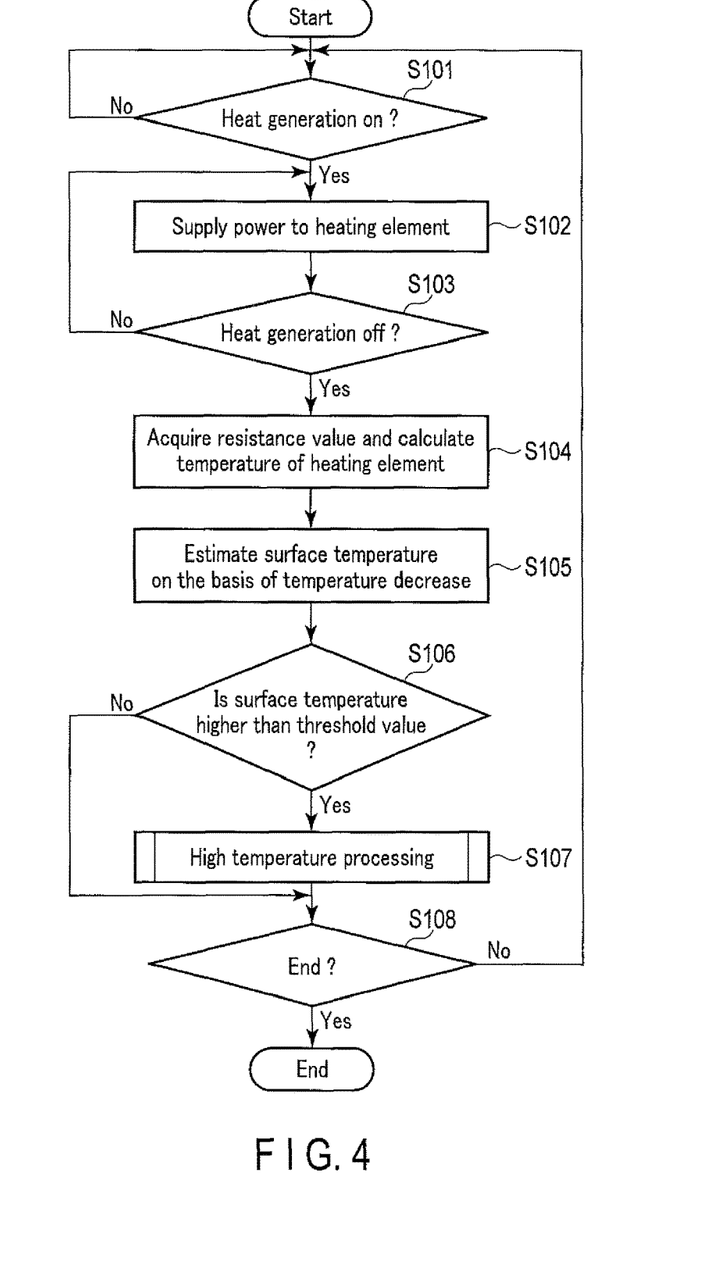
FIG. 4 is a flowchart showing one example of processing in a control device according to the one embodiment.

The operation of the control device 100 will further be described with reference to a flowchart shown in FIG. 4.

In step S101, the control section 110 determines whether or not the foot switch 310 switches on, i.e., whether or not to turn on the heat generation by the heating element 224. When it is determined that the heat generation is not turned on processing returns to step S101. That is, the control section 110 repeats the processing of step S101 until the foot switch 310 switches on. When it is determined in step S101 that the heat generation turns on, the processing advances to step S102.

In step S102, the control section 110 controls an operation of the heating element driving circuit 130 to supply the power to the heating element 224. As a result, the current flows through the heating element 224 and the heating element 224 generates heat. The heat generated by the heating element 224 is transferred to the treating portion 222 and the biological tissue in contact with the treating portion 222 is heated. At this time, the control section 110 executes feedback control of an output from the heating element driving circuit 130. That is, the control section 110 acquires, from, the temperature acquiring section 140, the temperature of the heating element 224 which is calculated on the basis of the resistance value of the resistance pattern, and executes the feedback control of the output from the heating element driving circuit 130 so that the temperature of the treating portion 222 becomes the target temperature on the basis of the temperature of the heating element 224.

In step S103, the control section 110 determines whether or not the foot switch 310 is turned off, i.e., the heat generation by the heating element 224 should be turned off. When it is determined that the heat generation is not turned off, the processing returns to step S102. That is, the power supply to the heating element 224 is continued. When it is determined in step S103 that the heat generation is turned off, the processing advances to step S104. At this time, the power supply to the heating element 224 stops.

In step S104, the control section 110 causes the temperature acquiring section 140 to acquire the temperature of the heating element 224 simultaneously with or immediately after the stop of the power supply to the heating element 224. That is, the temperature acquiring section 140 acquires a voltage value of the voltage applied to the heating element 224 and a current value of the current flowing at this time from the heating element driving circuit 130. The temperature acquiring section 140 calculates the resistance value of the resistance pattern of the heating element 224 on the basis of the acquired voltage value and current value. The temperature acquiring section 140 acquires information indicating a relation between the resistance value of the resistance pattern of the heating element 224 and the temperature of the heating element 224 which is stored in the storage section 120 via the control section 110, and the temperature acquiring section 140 calculates the temperature of the heating element 224 on the basis of the information. The temperature acquiring section 140 outputs the calculated temperature of the heating element 224 to the surface temperature estimating section 150. Such calculation of the temperature of the heating element 224 and the output of the temperature to the surface temperature estimating section 150 are performed at appropriate timings.

In step S105, the control section 110 causes the surface temperature estimating section 150 to estimate a temperature of the surface of the first holding member 212 as the surface temperature. Here, the temperature estimated as the surface temperature is a temperature of a portion different from a portion facing the second holding member 214 in the surface of the first holding member 212, and is, for example, a temperature of a portion of a back surface or a side surface of the first holding member 212. The surface temperature is calculated on the basis of the temperature change of the heating element 224 after the supply of the power to the heating element 224 is stopped.

Figure 5A:
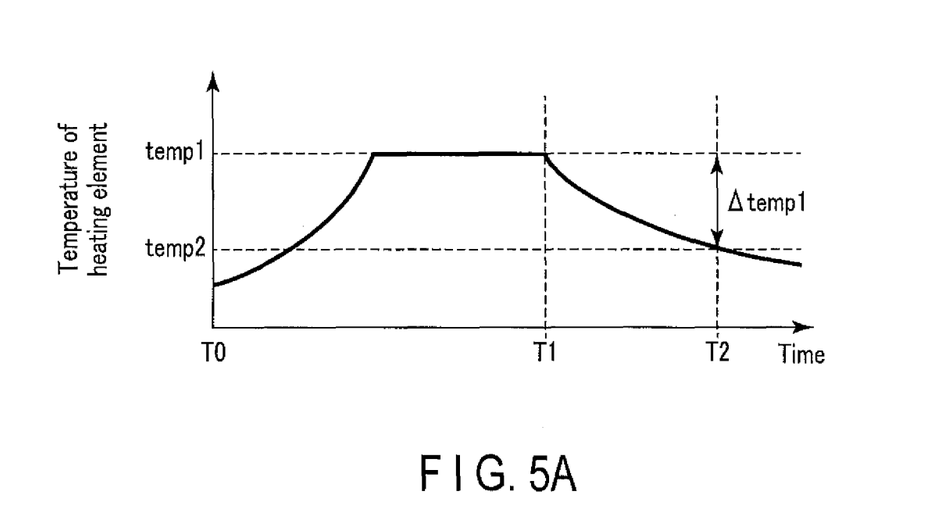
FIG. 5A is a view showing one example of a change of a temperature of a heating element to elapsed time.

FIG. 5A shows one example of the temperature change of the heating element 224 to elapsed time. At time T0, the power supply to the heating element 224 is started. At this time, the temperature of the heating element 224 rises with the elapsed time. Consequently, when the temperature of the heating element 224 reaches a first temperature temp1 that is the target temperature, the power to be supplied to the heating element 224 is adjusted by the control section 110, and the temperature of the heating element 224 is maintained at a first temperature temp1. It is defined that the power supply to the heating element 224 is stopped at time T1. At this time, the temperature of the heating element 224 decreases with the time. That is, the heat of the heating element 224 is transferred to the holding member main body 228 or the like and is radiated to the environment from the surface of the holding member main body 228, e.g., the back surface or the side surface of the first holding member 212, or the like.

In the example shown in FIG. 5A, the temperature of the heating element 224 becomes a second temperature temp2 at time T2. That is, in the example shown in FIG. 5A, from the time T1 to the time T2, the temperature of the heating element 224 decreases as much as a temperature difference Δtemp1 from the first temperature temp1 to the second temperature temp2. Here, Δtemp1=temp1−temp2.

Figure 5B:
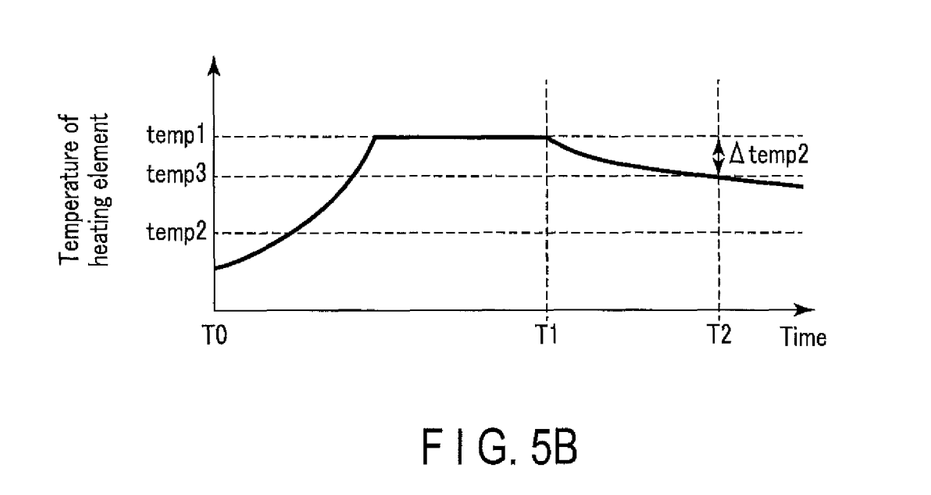
FIG. 5B is a view showing one example of a change of the temperature of the heating element to elapsed time.

FIG. 5B shows one example of the temperature change of the heating element 224 to the elapsed time in a case where the surface temperature such as the temperature of the back surface of the first holding member 212 is higher than that shown in FIG. 5A. Also in the case shown in FIG. 5B, the power supply to the heating element 224 is started at the time T0, the temperature of the heating element 224 is maintained at the first temperature temp1, and then at the time T1, the power supply to the heating element 224 is stopped. In the example shown in FIG. 53, from the time T1 to the time T2, the temperature of the heating element 224 decreases as much as a temperature difference Δtemp2 from the first temperature temp1 to a third temperature temp3. Here, Δtemp2=temp1−temp3. Δtemp2 is smaller than Δtemp1. That is, the higher the surface temperature is, the smaller the temperature decrease of the heating element 224 after the power supply to the heating element 224 is stopped per predetermined time becomes. In this way, when the temperature decrease of the heating element 224 to the elapsed time is measured, for example, the surface temperature of the back surface or the like can be estimated.

Transfer of the heat from a first region to a second region is represented by a heat conduction equation mentioned below. That is, Equation (1) of a quantity of the heat to be transferred per unit is established as follows:

$$Q/T=KS(\Delta \text{temp})/L=KS(\text{temp}A=\text{temp}B)/L \qquad (1),$$

where Q is a quantity of the heat to be transferred from the first region to the second region, K is a thermal conductivity of a heat transferring member, S is an area of a portion through which the heat transfers, L is a distance along which the heat transfers, T is elapsed time, tempA is a temperature of the first region, tempB is a temperature of the second region, and Δtemp is a temperature difference between the first region and the second region.

Here, the thermal conductivity K, the area S and the distance L of the whole first holding member 212 are beforehand obtained and stored in, for example, the storage section 120. When the temperature of the heating element 224 is acquired as the temperature tempA of the first region and the quantity Q/T of the heat to be transferred per unit time is acquired as the temperature decrease, for example, the temperature of the back surface can be estimated as the temperature tempB of the second region.

It is to be noted that the information of the thermal conductivity K, the area S and the distance L of the whole first holding member 212 can be acquired by, for example, experiments. The information of the thermal conductivity K, the area S and the distance L of the whole first holding member 212 may be stored in a memory disposed in the energy treatment tool 200. In this case, the control device 100 reads the information from the memory disposed in the energy treatment tool 200.

The temperature tempB of the second region which is the surface temperature of the first holding member 212 may be calculated by calculation on the basis of Equation (1) mentioned above. Furthermore, the temperature tempB of the second region may be obtained by referring a relation between the temperature tempB of the second region and each of the temperature tempA of the first region per unit time and the quantity Q/T of the heat to be transferred, which is stored, for example, as a table in the storage section 120.

As described above, the surface temperature estimating section 150 estimates the surface temperature on the basis of the temperature change of the heating element 224 after the power supply. The surface temperature estimating section 150 transmits the estimated temperature to the control section 110.

In step S106, the control section 110 determines whether or not the surface temperature estimated by the surface temperature estimating section 150 is higher than a predetermined threshold value. Here, the predetermined threshold value may be set to any degrees centigrade, but is set to, for example, 60° C. When it is determined that the surface temperature is not more than the predetermined threshold value, the processing advances to step S108. On the other hand, when the surface temperature is higher than the predetermined threshold value, the processing advances to step S107.

In step S107, the control section 110 performs high temperature processing. In the high temperature processing, the processing is performed so that the surface temperature does not heighten to cause any problems. The high temperature processing will be described later. After the high temperature processing, the processing advances to step S108.

In step S108, the control section 110 determines whether or not to end the processing. For example, when the input section 160 inputs an instruction to end the processing, the processing ends. When it is determined that the processing is ended, the processing ends. On the other hand, when it is determined that the processing is not ended, the processing returns to step S101.

Figure 6:
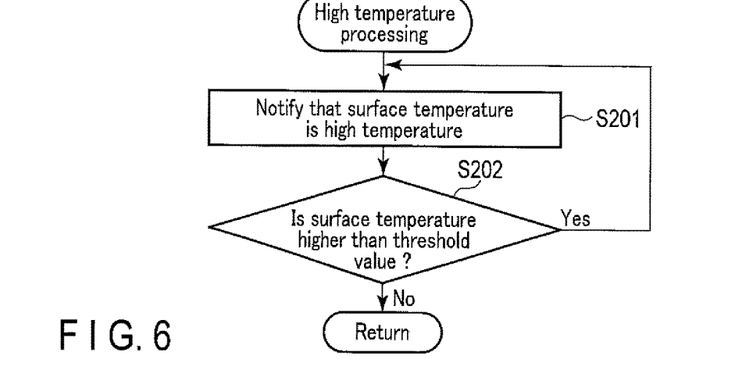
FIG. 6 is a flowchart showing one example of high temperature processing.

One example of the high temperature processing will be described with reference to a flowchart shown in FIG. 6. In the example shown in FIG. 6, the supply of the power to the heating element 224 is stopped until the surface temperature reaches the predetermined threshold value or less.

In step S201, the control section 110 causes the notification control section 170 to notify that the surface temperature is a temperature higher than a predetermined temperature. The notification control section 170 causes, for example, the display section 180 to display that the surface temperature is the high temperature and that due to the high temperature, the power is not supplied to the heating element 224. Furthermore, the notification control section 170 may output, from the speaker 190, voice indicating that the surface temperature is the high temperature and that due to the high temperature, the power is not supplied to the heating element 224. Afterward, the processing advances to step S202.

In step S202, the control section 110 determines whether or not the surface temperature is higher than the predetermined threshold value. When it is determined that the surface temperature is higher than the predetermined threshold value, the processing returns to step S201. Therefore, while the surface temperature is higher than the predetermined threshold value, it continues to be notified that the surface temperature is the high temperature without supplying the power to the heating element 224. When the surface temperature is not more than the predetermined threshold value in step S202, the processing returns to the processing described with reference to FIG. 4.

Another example of the high temperature processing will be described with reference to a flowchart shown in FIG. 7. In the example shown in FIG. 7, the power to be supplied to the heating element 224 is adjusted into a low level until the surface temperature reaches the predetermined threshold value or less.

In step S301, the control section 110 determines whether or not the foot switch 310 switches on and the heat generation is turned on. When it is determined that the heat generation is not turned on, the processing advances to step S307. On the other hand, when it is determined that the heat generation is turned on, the processing advances to step S302.

In step S302, the control section 110 causes the heating element driving circuit 130 to supply low power to the heating element 224. Here, the power to be supplied to the heating element 224 by the heating element driving circuit 130 has a level lower than that of the power supplied to the heating element 224 by the heating element driving circuit 130 in step S102 of the processing described with reference to FIG. 4. The supplied power is suppressed to the low level, whereby the rise of the surface temperature is suppressed.

In step S303, the control section 110 causes the notification control section 170 to notify that the output by the heating element 224 is the low level. By this notification, the user can know that the current output is the low level.

In step S304, the control section 110 determines whether or not to turn off the heat generation. When it is determined that the heat generation is not turned off, the processing returns to step S302. As a result, the supply of the low level power to the heating element 224 is continued. On the other hand, when it is determined that the heat generation is turned off, the processing advances to step S305. At this time, the power supply to the heating element 224 is stopped.

In step S305, the control section 110 causes the temperature acquiring section 140 to acquire the temperature of the heating element 224 on the basis of the resistance value of the resistance pattern of the heating element 224. In step S306, the control section 110 causes the surface temperature estimating section 150 to estimate the surface temperature on the basis of the temperature decrease of the heating element 224.

In step S307, the control section 110 determines whether or not the surface temperature is higher than the predetermined threshold value. When it is determined that the surface temperature is higher than the predetermined threshold value, the processing returns to step S301. On the other hand, when it is determined that the surface temperature is not more than the predetermined threshold value, the processing returns to the processing described with reference to FIG. 4.

Figure 7:
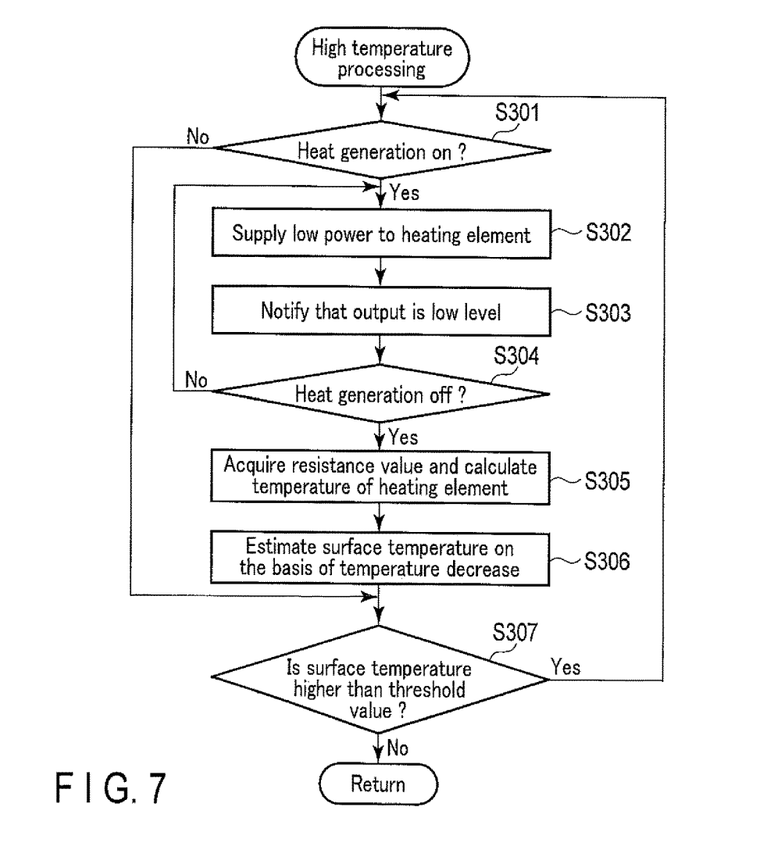
FIG. 7 is a flowchart showing another example of the high temperature processing.

According to the high temperature processing shown in FIG. 7, while the surface temperature is higher than the predetermined threshold value, the power supplied to the heating element 224 is suppressed to the low level, and when the surface temperature is not more than the predetermined threshold value, the processing returns to usual processing. It is to be noted that the power supplied in step S302 may be a constant power different from the usual supply power, a power obtained by multiplying the usual supply power by a predetermined coefficient, or a power corresponding to the surface temperature. It is preferable that the higher the surface temperature is, the smaller the power to be supplied becomes, so that the surface temperature becomes lower than the predetermined threshold value quickly.

As described above, according to the present embodiment, control is executed so that the surface temperature of the first holding member 212 does not heighten. In this case, the surface temperature is estimated on the basis of the temperature of the heating element 224 without being directly measured. Therefore, according to the present embodiment, it is not necessary to dispose a temperature sensor to measure the surface temperature separately from a mechanism to measure the temperature of the heating element. It is to be noted that it is necessary to acquire the temperature of the heating element, 224 for the control to maintain the temperature of the heating element 224 at the target temperature.

As described above, according to the present embodiment, the surface temperature can be acquired by a simple method while simplifying the configuration of the first holding member 212. Furthermore, by use of the acquired surface temperature, it is possible to avoid bad influences such as a failure of the energy treatment tool 200 due to the rise of the surface temperature of the first holding member 212 and a damage of the biological tissue due to the fact that the high-temperature back surface or the like unexpectedly comes in contact with the biological tissue. Furthermore, the estimating of the surface temperature on the basis of the temperature change of the heating element 224 produces effect in miniaturization of the first holding member 212.

It is to be noted that in the present embodiment, the temperature of the heating element 224 is acquired on the basis of an electric resistance value of the resistance pattern of the heating element 224. In this way, when the temperature is acquired on the basis of the resistance value, a temperature sensor is not required separately from the heating element 224. This produces effect in the miniaturization of the first holding member 212.

As described above, a temperature acquiring method of the heating element 224 is not limited to a method of acquiring the temperature on the basis of the resistance value of the resistance pattern of the heating element. The temperature sensor may be disposed in the vicinity of the heating element 224 to acquire temperature information of the heating element 224 from the temperature sensor.

Furthermore, in the above-mentioned embodiment, when the surface temperature is higher than the predetermined threshold value, the supply of the power to the heating element 224 may continue as usual, and it may only be notified that the surface temperature is high. The user who can recognize that the surface temperature is high can perform the treatment while being careful so that the back surface or the like does not come in contact with another tissue or the like.

Furthermore, in the above-mentioned embodiment, there has been described the example in which a heat generating mechanism such as the heating element 224 is only disposed in the first holding member 212, but the present invention is not limited to this embodiment, and the heat generating mechanism may also be disposed in the second holding member 214 in the same manner as in the first holding member 212.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A control device for an energy treatment tool including: (i) a first holding member with a holding surface configured to contact a biological tissue, (ii) a second holding member configured to open and close relative to the first holding member such that the biological tissue is held between the first holding member and the second holding member, and (iii) a heating element configured to generate heat corresponding to supplied power for heating the holding surface, the control device comprising:

at least one circuit or processor configured to:
 acquire a temperature of the heating element; and
 estimate a temperature of an objective surface as a surface temperature based on a change of the temperature of the heating element after supply of the power is stopped, wherein the objective surface is at least a part of an outer surface of the first holding member, the objective surface is different from a portion facing the second holding member, and the objective surface is separate from the heating element.

2. The control device according to claim 1, wherein the at least one circuit or processor is configured to acquire an electric resistance value of the heating element, and acquire the temperature of the heating element based on the electric resistance value.

3. The control device according to claim 1, wherein the at least one circuit or processor is configured to control the power to be supplied to the heating element based on the estimated surface temperature.

4. The control device according to claim 3, wherein the at least one circuit or processor is configured to:
notify that the surface temperature is higher than a predetermined threshold value, when the estimated surface temperature is higher than the predetermined temperature, and
stop the supply of the power to the heating element or to lower the supply of the power to the heating element, when the surface temperature is higher than the predetermined threshold value.

5. The control device according to claim 1, wherein the at least one circuit or processor is configured to estimate the surface temperature based on the temperature of the heating element and information including a thermal conductivity, a thickness and an area of the first holding member.

6. The control device according to claim 1, wherein the at least one circuit or processor is configured to control notification that the surface temperature is higher than a predetermined threshold value, when the estimated surface temperature is higher than the predetermined threshold value.

7. The control device according to claim 1, wherein the at least one circuit or processor is configured to estimate, as the surface temperature, a temperature of the objective surface, wherein the objective surface is a back surface that is a surface opposite to the holding surface of the first holding member, or a side surface.

8. An energy treatment system comprising:
an energy treatment tool including:
a first holding member with a holding surface configured to contact a biological tissue,
a second holding member configured to open and close relative to the first holding member such that the biological tissue is held between the first holding member and the second holding member, and
a heating element configured to generate heat corresponding to supplied power for heating the holding surface; and
a control device including at least one circuit or processor configured to:
acquire a temperature of the heating element, and
estimate a temperature of an objective surface as a surface temperature based on a change of the temperature of the heating element after supply of the power is stopped, wherein the objective surface is at least a part of an outer surface of the first holding member, the objective surface is different from a portion facing the second holding member, and the objective surface is separate from the heating element.

9. The energy treatment system according to claim 8, wherein
the at least one circuit or processor is configured to acquire an electric resistance value of the heating element, and acquire the temperature of the heating element based on the electric resistance value.

10. The energy treatment system according to claim 8, wherein
the energy treatment tool includes a temperature sensor that measures a temperature of the heating element, and
the at least one circuit or processor is configured to acquire the temperature of the heating element based on an output of the temperature sensor.

11. The energy treatment system according to claim 8, wherein the first holding member is provided with an insulating member which is disposed between the objective surface and the heating element.

* * * * *